US008530196B2

(12) United States Patent
Eberwine et al.

(10) Patent No.: US 8,530,196 B2
(45) Date of Patent: Sep. 10, 2013

(54) IN SITU CLONING FROM PATHOLOGICAL TISSUE SPECIMENS

(75) Inventors: James H. Eberwine, Philadelphia, PA (US); Max B. Kelz, Merion Station, PA (US)

(73) Assignee: The Trustees of the Univeristy of Pennsylvania, Philadelphia, PA (US)

( * ) Notice: Subject to any disclaimer, the term of this patent is extended or adjusted under 35 U.S.C. 154(b) by 621 days.

(21) Appl. No.: 11/784,677

(22) Filed: Apr. 9, 2007

(65) Prior Publication Data

US 2009/0023593 A1    Jan. 22, 2009

Related U.S. Application Data

(60) Provisional application No. 60/790,382, filed on Apr. 7, 2006.

(51) Int. Cl.
*C12P 19/34* (2006.01)

(52) U.S. Cl.
USPC ......................................................... 435/91.2

(58) Field of Classification Search
USPC ......................................................... 435/91.2
See application file for complete search history.

(56) References Cited

U.S. PATENT DOCUMENTS

| | | | |
|---|---|---|---|
| 5,672,696 A | 9/1997 | Wang et al. | |
| 5,750,340 A | 5/1998 | Kim et al. | 435/6 |
| 5,856,089 A | 1/1999 | Wang et al. | 435/6 |
| 5,981,190 A * | 11/1999 | Israel | 435/6 |
| 6,165,723 A | 12/2000 | Shah et al. | 435/6 |
| 6,287,778 B1 * | 9/2001 | Huang et al. | 506/4 |
| 6,534,266 B1 | 3/2003 | Singer | 435/6 |
| 2002/0192702 A1 | 12/2002 | Kononen et al. | |
| 2003/0040035 A1 | 2/2003 | Slamon et al. | 435/40.5 |
| 2005/0142589 A1 | 6/2005 | Broide et al. | 435/6 |
| 2006/0141502 A1 * | 6/2006 | Capodieci et al. | 435/6 |
| 2007/0148636 A1 * | 6/2007 | Song et al. | 435/5 |

OTHER PUBLICATIONS

Bonin et al., 2005, DNA and RNA Obtained from Bouin's Fixed Tissues, *Journal of Clinical Pathology*, vol. 58, pp. 313-316.
Greer et al., 1991, "PCR Amplification from Paraffin-Embedded Tissues: Recommendations on Fixatives for Long-Term Storage and Prospective Studies," *PCR Methods Appl.*, vol. 1, pp. 46-50.
Hilton et al., 1993, "Demonstration of Coxsackie Virus RNA in Formalin-Fixed Tissue Sections from Childhood Myocarditis Cases by in Situ Hybridization and the Polymerase Chain Reaction," *Journal of Pathology*, vol. 170, pp. 45-51.
Levsky et al., 2002, *Science*, vol. 297, pp. 836-840.
Long, 1998, "In-situ polymerase chain reaction: foundation of the technology and today's options," *Eur. J. Histochem.* vol. 42, pp. 101-109.
Souvenir et al., 2003, "Selecting Degenerate Multiplex PCR Primers," *Proceedings of the 3rd International Workshop on Algorithms in Bioinformatics (WABI)*.

* cited by examiner

*Primary Examiner* — Cynthia Wilder
(74) *Attorney, Agent, or Firm* — Riverside Law LLP

(57) ABSTRACT

The present invention pertains to methods related to cloning nucleic acids from biological samples, particularly pathological tissue samples. This method includes hybridizing a population of oligonucleotide sequence probes comprising degenerate sequence tags to a fixed tissue, isolating the hybridized oligonucleotide sequence probes and amplifying the sequence tags in the hybridized oligonucleotide sequence probes. This method can be utilized to identify genes associated with disease and to quantitate the expression of disease-related transcripts. The method can also be used to identify truncated mRNAs.

17 Claims, 5 Drawing Sheets

```
TCGAGG TTTTC TATTC CCCCA AGAGC CCAATTGG CATTT GTTTC GGGGG G?AGG CC
TCGAGG ACCTC CTATG GCGCC TTGTA CCAATTGG GGGAT GGCAA TGTGA TGTAC CC
TCGAGG ACTGG CCCCC CATAT AACAA CCAATTGG GGGAT GCTTG GTATA GACGA CC
TCGAGG ATTAT CTCCA CGTCA ACTGC CCAATTGG TGTTT GACAG TCTTT CGTGT CC
TCGAGG ACACG CACCC TGACC ATACC CCAATTGG AGAAT GTCTG TTTG? GAATG CC
```

IN SITU CLONING FROM PATHOLOGICAL TISSUE SPECIMENS

CROSS REFERENCE TO RELATED APPLICATIONS

This application claims the benefit pursuant to 35 U.S.C. §119(e) to U.S. provisional patent application 60/790,382, which was filed on Apr. 7, 2006 and which is incorporated herein by reference in its entirety.

BACKGROUND OF THE INVENTION

Advancements in the understanding of gene expression and epidemiology combined with developments in technology have allowed for the correlation of genetic expression with, for example, disease states. An accurate correlation may enable risk assessment for an individual based on the expression profile of his/her individual cells or tissue. Further, drug screening and other research based protocols may quickly generate data in tissue samples that can be extended to develop treatments for human disease.

There is an abundance of specimens resulting from the pathological analysis of the disease; however, there are drawbacks to the typical methodologies available for evaluating them. For example, it is not always possible in the clinical setting to work on cell lines or tissue as soon as they are available and, consequently, they are often preserved in a fixative that permits the retention of cellular morphology and cellular constituents. The most common type of fixative is a cross-linking fixative that chemically couples proteins, RNAs, DNAs and small molecules in an insoluble matrix. Efforts have been made to isolate RNA from such fixed tissue in order to, for instance, analyze RNA populations. Some commercial products, for instance, Paradise™ Reagent System (Arcturus, Mountain View, Calif.), are available. These efforts, however, have universally found the RNA to be quite short. It is believed the short RNAs likely represent the regions of RNA between the chemical cross-linked residues. As a result of their short length, these short sequences are difficult to isolate and to analyze. Furthermore, amplification of these RNAs is often needed, and the amplification process is also impeded by the short length of the isolated RNAs.

Another drawback is that methods that require disaggregation of the sample, such as Southern, Northern, or Western blot analysis, are rendered less accurate by dilution of the malignant cells by the normal or otherwise non-malignant cells that are present in the same sample. Furthermore, the resulting loss of tissue architecture precludes the ability, for example, to correlate the presence of genetic abnormalities with malignant cells in a context that allows morphological specificity. This issue is particularly problematic in tissue types known to be heterogeneous, such as in human breast carcinoma, where a significant percentage of the cells present in any given area may be non-malignant.

In situ hybridization (ISH) is a powerful and versatile tool for the detection and localization of nucleic acids (DNA and RNA) within cell or tissue preparations. See, for instance, U.S. Pat. Nos. 5,750,340 and 6,165,723. In ISH, labeled nucleic acids (DNA or RNA) are hybridized to chromosomes, DNA or mRNAs in cells which are immobilized on microscope glass slides (In Situ Hybridization: Medical Applications (eds. G. R. Coulton and J. de Belleroche), Kluwer Academic Publishers, Boston (1992); In Situ Hybridization: In Neurobiology; Advances in Methodology (eds. J. H. Eberwine, K. L. Valentino, and J. D. Barchas), Oxford University Press Inc., England (1994); In Situ Hybridization: A Practical Approach (ed. D. G. Wilkinson), Oxford University Press Inc., England (1992)). Numerous non-isotopic systems have been developed to visualize labeled DNA probes including, for example, a) fluorescence-based direct detection methods, b) digoxigenin- and biotin-labeled DNA probes coupled with fluorescence detection methods, and c) digoxigenin- and biotin-labeled DNA probes coupled with antibody-enzyme detection methods. When fluorescence-labeled nucleic acid (DNA or RNA) probes are hybridized to cellular DNA or RNA targets, the hybridized probes can be viewed directly using a fluorescence microscope. By using multiple nucleic acid probes with different fluorescence colors, simultaneous multicolored analysis (i.e., for multiple genes or RNAs) can be performed in a single step on a single target cell (Levsky et al., 2002, Science 297:836-840). Fluorochrome-directly labeled nucleic acid probes eliminate the need for multi-layer detection procedures (e.g., antibody-based system), which allows for faster processing and also reduces non-specific background signals. Therefore, fluorescence in situ hybridization (FISH) has become an increasingly popular and valuable tool in both basic and clinical sciences. ISH also been combined with polymerase chain reaction (PCR) to amplify, for instance, low abundance nucleic acid (see, e.g., Long, 1998, Eur. J. Histochem. 42:101-109). In situ PCR involves first amplifying, in situ, specific gene sequences, followed by in situ hybridization to detect the amplified sequences.

Through the use of labeled DNA or RNA probes, the ISH technique provides a high degree of spatial information in locating specific DNA or RNA target within individual cells or chromosomes. ISH is widely used for research and potentially for diagnosis in the areas of prenatal genetic disorders, and molecular cytogenetics. In the general area of molecular biology, ISH is used to detect gene expression, to map genes, to identify sites of gene expression, to localize target genes, and to identify and localize various viral and microbial infections. Currently, the application of the ISH technology research is being expanded into tumor diagnosis, preimplantation genetic diagnosis for in vitro fertilization, evaluation of bone marrow transplantation, and analysis of chromosome aneuploidy in interphase and metaphase nuclei.

U.S. Pat. No. 5,856,089 describes in situ hybridization methods using nucleic acid probes for single copy nucleic acid sequences to detect chromosomal structural abnormalities in fixed tissue obtained from a patient suspected of having a chromosomal structural abnormality. The methods include the use of bisulfite ion on the fixed cells.

U.S. Pat. No. 5,672,696 describes preparation of a sample for a gene analysis or high-purity nucleic acid suitable for gene amplification from a fixed, paraffin-embedded tissue sample comprising heating an aqueous suspension containing a surfactant having a protein-denaturation action and a deparaffinized tissue sample obtained from a paraffin-embedded tissue sample at 60° C. or higher.

U.S. Pat. No. 6,534,266 describes an in situ hybridization method for detecting and specifically identifying transcription of a multiplicity of different target sequences in a cell. The method includes assigning a different bar code to at least five target sequences, with each target sequence containing at least one, predetermined subsequence. Each bar code contains at least one fluorochrome, and at least one bar code comprises at least two different, spectrally-distinguishable fluorochromes. A probe set specific for each target sequence is provided in the method. Each probe set contains a hybridization probe complementary to each subsequence in the target sequence. Each probe is labeled with a fluorochrome, and the fluorochromes in each probe set collectively correspond to the bar code for the target sequence of that probe set.

U.S. Patent Application Publication No. 2005/0142589 discloses a method of detecting the relative amounts of multiple target messenger RNA's in a microscopy sample using in situ hybridization and sets of designed oligonucleotides probes. Each set comprises two or more oligonucleotides that will hybridize to a particular nucleic acid sequence of interest. The method permits the hybridization signal to be increased, for instance, for targets known or suspected to be in low abundance, by increasing the number of probes in a set that will hybridize to the target.

Spotted chip expression microarrays have been used extensively to detect the presence or absence of multiple specific mRNAs simultaneously in tissue. However, to date, the effective application of this technique has been limited to fresh frozen tissue. An easy application utilizing paraffin-embedded or other fixed-treated tissue spotted chip expression microarrays has not been described to date. See, for example, U.S. Patent Publication Nos. 20030040035 and 20020192702. Because many of the cell lines and tissue available for scientific or medical study have been fixed, the ability to effectively use spotted chip arrays on fixed-treated cell lines and tissue would be of great potential value in (1) the discovery of the molecular mechanisms of the cell and its surrounding tissue in health and disease, (2) the creation of tests diagnostic of disease, (3) the creation of treatments therapeutic for disease, and (4) the identification of agents that are toxic to cells.

There exists, therefore, a need in the art for a method utilizing fixed pathological specimens as a resource for studying disease. This need arises, in part, from the notion that an understanding of the gene expression patterns of certain diseases, such as cancer, may be central to successful management and treatment of diseases. The present invention fulfills this need by providing a procedure for the in situ cloning of RNAs from tissue specimens that have been fixed in any manner that retains RNA in a specimen.

SUMMARY OF THE INVENTION

The invention provides a method of cloning a nucleic acid from a biological sample. The method comprises the steps of (a) providing a population of oligonucleotide sequence probes, wherein each of the oligonucleotide sequence probe comprises a sequence tag flanked by a 5'-end extension sequence and a 3'-end extension sequence, wherein the sequence tag is a degenerate sequence and wherein at least one of the 5'-end extension sequence and the 3'-end extension sequence comprises a detection sequence; (b) hybridizing the population of oligonucleotide sequence probes with the nucleic acid in the biological specimen, thereby forming a population of hybridized oligonucleotide sequences probes and a population of unhybridized oligonucleotide sequence probes; (c) washing away the population of unhybridized oligonucleotide sequence probes; and (d) isolating the population of hybridized oligonucleotide sequence probes thereby forming an isolated population of hybridized oligonucleotide sequence probes, thereby cloning the nucleic acid from the biological sample. In some embodiments, the biological sample is from a human. In some embodiments, at least one of the 5'-end extension sequence and the 3'-end extension sequence comprises a detection sequence.

In one embodiment, the method of cloning a nucleic acid further comprises amplifying the population of isolated hybridized oligonucleotide sequence probes to produce a population of amplified fragments comprising sequence tags. The amplifying step may comprise the polymerase chain reaction. In one aspect of this embodiment, the method further comprises hybridizing the population of amplified fragments comprising sequence tags to a microarray, thereby determining the sequences of the sequence tags. Optionally, the method further comprises comparing sequences of the sequence tags to a database of gene sequences, thereby identifying genes comprising said sequence tags.

In another aspect of this embodiment, the sequence tags in the population of amplified fragments are sequenced. In some embodiments, the 5'-end extension sequence and the 3'-end extension sequence each comprise a restriction site for a class II restriction endonuclease or a homing endonuclease. In some embodiments, the population of amplified fragments comprising sequence tags is cleaved with the class II restriction endonuclease or homing endonuclease to produce cleaved fragments, and the cleaved fragments are subcloned into a vector. Optionally, the cleaved fragments comprising sequence tags are ligated together prior to the subcloning step. In some aspects of this embodiment, the method further comprises comparing sequences of the sequence tags to a database of gene sequences, thereby identifying one or more genes comprising the sequence tags.

The invention provides a method of obtaining a cell or tissue of interest from a biological specimen, the method comprising the steps of (a) providing a population of oligonucleotide sequence probes, wherein each of the oligonucleotide sequence probe comprises a sequence tag flanked by a 5'-end extension sequence and a 3'-end extension sequence, wherein the sequence tag is a degenerate sequence and wherein at least one of the 5'-end extension sequence and the 3'-end extension sequence comprises a detection sequence; (b) hybridizing the population of oligonucleotide sequence probes with the nucleic acid in the biological specimen, thereby forming a population of hybridized oligonucleotide sequences probes and a population of unhybridized oligonucleotide sequence probes; (c) washing away the population of unhybridized oligonucleotide sequence probes; (d) annealing a detection oligonucleotide comprising a detectable label to at least one of the 5'-end extension sequence and the 3'-end extension sequence of each of the oligonucleotide sequence probe, wherein the detection oligonucleotide is complementary to a detection sequence; (e) detecting the detectable label to identify a cell or tissue comprising hybridized oligonucleotide sequence probes; and (f) separating said cell or tissue that comprises the detectable label from cells or tissue that do not comprise the detectable label, wherein step (d) is performed before or after step (b). In some aspects of this embodiment, the detectable label is a fluorescent label.

In some embodiments of the method, the biological sample is a pathological sample. The biological sample may be fixed. Methods of fixation for preparing fixed biological samples include formaldehyde, Bouin's, xylene and an ethanol precipitating fixative. In some embodiments, the fixed biological sample is treated with a permeabilization agent prior to the hybridizing step. The permeabilization agent is selected from the group consisting of proteinase K, pronase and triethanolamine in some embodiments.

In yet another embodiment, the method of the invention is employed to clone nucleic acid from a test biological sample and a control biological sample, and the cloned nucleic acid of the test sample is compared to the cloned nucleic acid of the control sample to identify differentially expressed genes. Preferably, the biological sample is from a human. In some embodiments, the test biological sample and the control biological sample are fixed tissue samples. In some embodiments, the fixed tissue samples are fixed by a method of fixation selected from the group consisting of formaldehyde, Bouin's, xylene, ethanol and methanol.

In another embodiment, the method of the invention is used to identifying a gene expressed in the sample comprising RNA from a subject and detect a pathological condition or a susceptibility to a pathological condition based on a change of expression of a gene in the sample compared to a healthy subject. Preferably, the subject is human.

In another embodiment, the method of the invention is used to identify a truncated mRNA by assessing the relative amounts of oligonucleotide sequence probes that hybridize to two different regions of an mRNA.

Kits useful in practicing the methods of the invention are also provided. In one embodiment, a kit for identifying a nucleic acid in a biological specimen of an organism of interest comprises an oligonucleotide sequence probe, wherein said oligonucleotide sequence probe comprises, in 5' to 3' order, a first sequence element comprising a sequence of about 10 to about 22 nucleotides that is not found in the genome of the organism of interest, a second sequence element that is a degenerate sequence and is about 18 to about 28 nucleotides long, and a third sequence element that comprises a sequence of about 10 to about 22 nucleotides that is not found in the genome of the organism of interest; wherein the first sequence element and the third sequence element are not identical and further wherein the oligonucleotide sequence probe is about 36 to about 200 nucleotides long; a first primer and a second primer, wherein the first primer comprises a sequence that is identical to at least about 8 consecutive nucleotides of the first sequence element and wherein the second primer comprises a sequence that is 100% complementary to at least about 8 consecutive nucleotides of the third sequence element; and an instructional material.

Also provided is a kit for identifying a nucleic acid in a human biological specimen. The kit comprises an oligonucleotide sequence probe, wherein the oligonucleotide sequence probe comprises, in 5' to 3' order, a first sequence element comprising a sequence of about 18 to about 22 nucleotides that is not found in the human genome, a second sequence element that is a degenerate sequence and is about 18 to about 28 nucleotides long, and a third sequence element that comprises a sequence of about 18 to about 22 nucleotides that is not found in the human genome; wherein the first sequence element and the third sequence element are not identical and further wherein the oligonucleotide sequence probe is about 54 to about 200 nucleotides long; a first primer and a second primer, wherein the first primer comprises a sequence that is identical to at least about 15 consecutive nucleotides of the first sequence element and wherein the second primer comprises a sequence that is 100% complementary to at least about 15 consecutive nucleotides of the third sequence element; and an instructional material.

In some embodiments of the kits, the oligonucleotide sequence probe further comprises: a fourth sequence element of about 10 to about 30 nucleotides that comprises a first restriction site, wherein the fourth sequence element is between the first and second sequence elements; and a fifth sequence element of about 10 to about 30 nucleotides that comprises a second restriction site, wherein the fifth sequence element is between the second and third sequence elements.

In some embodiments of the kits, the first restriction site and the second restriction site are Fok I sites. In other embodiments, the sites are I-CeuI sites.

In some embodiments of the kits, at least one of the first and second primers comprises biotin. In some embodiments, at least one of the first and second primers comprises a detectable label. In some aspects, the detectable label is selected from the group consisting of a chromogenic moiety, a radioactive moiety and a fluorescent moiety. In some embodiments, one of the first and second primers comprises biotin and the other of the first and second primers comprises a detectable label. In some embodiments of the kits, at least one of said first and second primers comprises one or more aminoallyl-substituted nucleotides.

The invention further provides a composition, the composition comprising an oligonucleotide sequence probe, wherein the oligonucleotide sequence probe comprises a sequence tag flanked by a 5'-end extension sequence and a 3'-end extension sequence, wherein the sequence tag is a degenerate sequence and wherein at least one of the 5'-end extension sequence and the 3'-end extension sequence comprises a detection sequence. A composition comprising a population of oligonucleotide sequence probes is also provided.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 7A and 7B, is a series of two images of the fluorescence from a section of a cDNA microarray. Both images are of the same section of the array. In FIG. 7A, a population of oligonucleotide sequence probes, which were not hybridized in situ, were PCR amplified and hybridized to the array. In FIG. 7B, a population of oligonucleotide sequence probes recovered from in situ hybridization to cortical cells was PCR amplified and hybridized to the array.

DETAILED DESCRIPTION OF THE INVENTION

Figure 1:
FIG. 1 is a schematic illustration of an embodiment of an oligonucleotide sequence probe. The segments having vertical hatching comprise detection sequences. The white segments comprise a restriction enzyme site. The segment having zigzag hatching is a sequence tag.

The present invention is based, in part, on the discovery that RNA sequences in tissue samples can be specifically identified, and RNA amounts can be quantified using in situ hybridization of a population of oligonucleotides comprising a degenerate sequence, referred to herein as a "sequence tag" and at least one unique detection sequence. Advantageously, the method does not rely on extraction of cellular RNA from a tissue sample, nor does it rely on in situ PCR amplification. Oligonucleotides that specifically hybridize to nucleic acid in a tissue sample are isolated, amplified, and the sequences of the sequence tags contained within are determined. The genes containing the sequences thus determined may be identified, for instance, by comparison to public databases of expressed sequences. The method of the invention, also referred to herein as "PCR of Anatomically Cloned Expressed Sequence Tags" (PACES), is a robust method for amplifying all cellular RNAs and offers improvements over existing methodologies for RNA amplification. By way of a non-limiting example, the method reduces the problems of template sequence and concentration artifacts typical of traditional PCR methods because the amplicons produced in the method of the invention are of equal size. Furthermore, the design of the oligonucleotides used in the hybridization step reduces the sequence differences among different oligonucleotides, which therefore reduces template size skewing. The method also has fewer steps than techniques such as aRNA amplification and, consequently, may provide a higher yield.

The method may be used in a myriad of applications. For instance, the method permits the easy molecular characterization of gene expression in any disease state and pathological tissue specimen. The method may be used for in vitro detection of a pathological condition or a susceptibility to a pathological condition in a subject, based on the presence or absence of expression or the increase or decrease in expression compared to expression in normal tissue, of one or more genes in a sample. In one embodiment, the method is used to test for the presence of a viral pathogen in a sample for which the infection status is unknown, or for a pathogen unknown at the time the sample was generated. Viral pathogens may be identified, for instance, by using microarrays containing sequences of known genes in known pathogens. In another embodiment, the application is particularly useful for samples, such as fossil specimens, for which intact RNA samples are not available. Advantageously, the method may be used with fixed tissue samples, regardless of the means of fixing. This advantage enables the use of archival tissue samples, thus permitting retrospective analysis. This is particularly advantageous, given the vast number of such archival tissue samples for which there are known clinical progression and outcomes. For instance, gene expression profiles in archival samples of breast cancer tissue from patients whose disease is known to have metastasized quickly may be generated using the inventive method to identify possibly relevant genes that are over- or under-expressed compared to normal breast tissue and that may be related to rapid metastasis of breast cancer.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

As used herein, each of the following terms has following meaning.

The articles "a" and "an" are used herein to refer to one or to more than one (i.e. to at least one) of the grammatical object of the article. By way of example, "an element" means one element or more than one element.

As used herein, the term "adjacent" is used to refer to nucleotide sequences which are directly attached to one another, having no intervening nucleotides. By way of example, the pentanucleotide 5'-AAAAA-3' is adjacent the trinucleotide 5'-TTT-3' when the two are connected thus: 5'-AAAAATTT-3' or 5'-TTTAAAAA-3', but not when the two are connected thus: 5'-AAAAACTTT-3'.

As used herein, the term "affected cell" refers to a cell of a subject afflicted with a disease or disorder, which affected cell has an altered phenotype, genotype and/or gene expression profile relative to a subject not afflicted with a disease or disorder.

Cells or tissue are "affected" by a disease or disorder if the cells or tissue have an altered phenotype, genotype and/or gene expression profile relative to the same cells or tissue in a subject not afflicted with a disease or disorder.

"Amplification" refers to any means by which a polynucleotide sequence is copied and thus expanded into a larger number of polynucleotide molecules, e.g., by reverse transcription, polymerase chain reaction, and ligase chain reaction, among others.

As used herein, "cloning a nucleic acid" refers to obtaining or isolating at least one copy of a nucleic acid or of a sequence complementary to a nucleic acid, either of which may represent a portion of a larger nucleic acid. A "portion of a nucleic acid" comprises at least about 5 nucleotides, and preferably at least about 10 nucleotides.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

An "mRNA-coding region" of a gene consists of the nucleotide residues of the coding strand of the gene and the nucleotide residues of the non-coding strand of the gene which are homologous with or complementary to, respectively, an mRNA molecule which is produced by transcription of the gene. It is understood that, owing to mRNA processing which occurs in certain instances in eukaryotic cells, the mRNA-coding region of a gene may comprise a single region or a plurality of regions separated from one another in the gene as it occurs in the genome. Where the mRNA-coding region of a gene comprises separate regions in a genome, "mRNA-coding region" refers both individually and collectively to each of these regions.

A "coding region" of an mRNA molecule consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g. amino acid residues in a protein export signal sequence).

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, "dehybridizing" refers to melting or disrupting the base pairing between complementary strands of nucleic acid. For instance, a double-stranded DNA molecule is dehybridized when the base pairing between the two strands is disrupted and the molecule is separated into two separate molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, are reduced.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A first region of an oligonucleotide "flanks" a second region of the oligonucleotide if the two regions are adjacent one another or if the two regions are separated by no more than about 1000 nucleotide residues, and preferably no more than about 100 nucleotide residues.

A "genomic DNA" of a human patient is a DNA strand which has a nucleotide sequence homologous with a gene of the patient. By way of example, both a fragment of a chromosome and a cDNA derived by reverse transcription of a human mRNA are genomic DNAs.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator www(dot)ncbi(dot)nlm(dot)nih (dot)gov/BLAST. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See www(dot)ncbi(dot)nlm(dot)nih(dot)gov.

The percent identity between two sequences can be determined using techniques similar to those described above, with or without allowing gaps. In calculating percent identity, typically exact matches are counted.

As used herein, the term "imaging agent" means a composition of matter which, when delivered to a cell, facilitates detection of the cell. Numerous imaging agents are known and described in the literature. By way of example, enzymes, such as β-galactosidase, which are capable of catalyzing a reaction involving a chromogenic substrate may be used. Further by way of example, compounds, the presence of which may be directly detected may be used, such as compounds which emit gamma radiation or which fluoresce, which may be detected using an appropriate detection apparatus may be used.

As used herein, an "instructional material" includes a publication, a recording, a diagram, or any other medium of expression which can be used to communicate the usefulness of the composition for its designated use in the method of the invention. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

A "microarray" is a linear or two-dimensional array of preferably discrete regions, each having a defined area, formed on the surface of a solid support such as, but not limited to, glass, plastic, or synthetic membrane. The density of the discrete regions on a microarray is determined by the total numbers of immobilized polynucleotides to be detected on the surface of a single solid phase support, preferably at least about 50/cm², more preferably at least about 100/cm², even more preferably at least about 500/cm², but preferably below about 1,000/cm². Preferably, the arrays contain less than about 500, about 1000, about 1500, about 2000, about 2500, or about 3000 immobilized polynucleotides in total.

As used herein, a "DNA microarray" is an array of oligonucleotides or polynucleotides placed, for instance, on a chip or other surface and used to hybridize to amplified or cloned polynucleotides from a sample. The phrase encompasses three-dimensional microarrays as well. Since the position of each particular group of oligonucleotides or polynucleotides in the array is known, the identities of a sample of polynucleotides can be determined based on their binding to a particular position in the microarray. A cDNA microarray comprises oligonucleotides or polynucleotides having sequences from expressed sequences.

A third primer is "nested" with respect to a first primer and a second primer if amplification of a region of a first oligonucleotide using the first primer and the second primer yields a second oligonucleotide, wherein the third primer is complementary to a portion of the second oligonucleotide, wherein the portion of the second oligonucleotide does not include a nucleotide residue at an end of the second oligonucleotide.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well as a coding function.

A "portion" of a polynucleotide means at least about eighteen sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with a detectable label, e.g., chromogenic, radioactive, or fluorescent moieties and used as detectable moieties. Examples of fluorescent moieties include, but are not limited to, rare earth chelates (europium chelates), Texas Red, rhodamine, fluorescein, dansyl, phycocrytherin, phycocyanin, spectrum orange, spectrum green, and/or derivatives of any one or more of the above. Other detectable moieties include digoxigenin and biotin.

As used herein, a "sequencing primer" is an oligonucleotide primer which is complementary to at least a portion of a polynucleotide and which can be elongated by a DNA or RNA polymerizing enzyme such as DNA polymerase, whereby binding of the sequencing primer to the polynucleotide and elongation of the primer using methods well known in the art yields an oligonucleotide transcript which is complementary to at least a part of the polynucleotide.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with a detectable label, e.g., chromogenic, radioactive, or fluorescent moieties and used as detectable moieties. Examples of fluorescent moieties include, but are not limited to, rare earth chelates (europium chelates), Texas Red, rhodamine, fluorescein, dansyl, phycocrytherin, phycocyanin, spectrum orange, spectrum green, and/or derivatives of any one or more of the above. Other detectable moieties include digoxigenin and biotin.

A first oligonucleotide anneals with a second oligonucleotide with "high stringency" if the two oligonucleotides anneal under conditions whereby only oligonucleotides which are at least about 75%, and preferably at least about 90% or at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g. Sambrook et al., 2001, Molecular Cloning: A Laboratory Manual, Cold Spring Harbor Laboratory Press, Cold Spring Harbor, N.Y.).

A "restriction site" is a portion of a double-stranded nucleic acid which is recognized by a restriction endonuclease.

A portion of a double-stranded nucleic acid is "recognized" by a restriction endonuclease if the endonuclease is capable of cleaving both strands of the nucleic acid at a specific location in the portion when the nucleic acid and the endonuclease are contacted. Restriction endonucleases, their cognate recognition sites and cleavage sites are well known in the art. See, for instance, Roberts et al., 2005, Nucleic Acids Research 33:D230-D232.

As used herein, an "oligonucleotide sequence probe" refers to an oligonucleotide comprising a sequence tag flanked by a 5'-end extension and a 3'-end extension and where the 5-end extension and the 3'-end extension comprise detection sequences. An oligonucleotide sequence probe is used in the method of the invention to hybridize to a nucleic acid in a tissue sample from an organism of interest.

As used herein, a "sequence tag" is the portion of the oligonucleotide sequence probe that may hybridize to a complementary sequence in a nucleic acid in a tissue sample. "Sequence tag" is used interchangeably with "PACES tag."

As used herein, a "detection sequence" is a sequence that is not found in the genome of the organism of interest from which the tissue sample is obtained.

As used herein, a "detection oligonucleotide" is a detectably-labeled oligonucleotide that is complementary to a detection sequence. An oligonucleotide sequence probe comprising the detection sequence may therefore be detected by hybridizing a detection oligonucleotide to the oligonucleotide sequence probe.

As used herein, a "population" of oligonucleotide sequence probes refers to a pool of two or more oligonucleotide sequence probes having different sequence tags.

As used herein, a "degenerate sequence" refers to sequence in which at one or more of the nucleotide positions, there are two or more types of nucleotides. By way of a non-limiting example, 5'-GC(A/G)CTGG-3' is a degenerate sequence because at position 3 in the sequence, the nucleotide is either an A or a G.

A "subject" of diagnosis or treatment is any animal, and is preferably a mammal, including a human. Non-human mammals subject to diagnosis or treatment include, for example, primates, sheep, cattle, goats, dogs, cats, and horses.

A tissue "normally comprises" a cell if one or more of the cells are present in the tissue in an animal not afflicted with a disease or disorder.

An "internal" tissue of an animal is a tissue which is normally located beneath the epidermis of the animal, within the animal's body.

As used herein, a "pathological sample" is a biological sample from a subject having or suspected of having a disease, disorder or condition. Pathological specimens, include, but are not limited to, histological tissue sections and/or other biological preparations such as tissue culture cells and PAP smears. Pathological samples are commonly used in diagnostic pathology.

As used herein, a "fixed sample" is a sample that has been treated so as to preserve the structural organization of cells and tissues in the sample in as close a life-like state as possible for subsequent examination, for instance, by light or electron microscope. Fixation typically arrests autolysis and bacterial decomposition and stabilizes the structural organization of cellular and tissue constituents so that they withstand the subsequent stages of tissue processing.

As used herein, a "permeabilization agent" is a chemical that enables a probe access to the intracellular constituents of a cell.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

DESCRIPTION OF THE INVENTION

The method of the invention, called PCR of Anatomically Cloned Expressed Sequence Tags or "PACES", employs an oligonucleotide sequence probe that comprises a sequence tag located between a 5'-end extension and a 3'-end extension. The oligonucleotide sequence probe may be about 38 to about 200 nucleotides in length, and more preferably about 90 to about 150 nucleotides. In one embodiment, the oligonucleotide sequence probe is 100 nucleotides in length. Advantageously, this relatively short length favors the successful penetration of tissue by the probe. The oligonucleotide sequence probes may be generated by any method known to the skilled artisan. Preferably, the oligonucleotide sequences probes are chemically synthesized.

The 5'-end extension and 3'-end extension comprise detection sequences. A detection sequence is a sequence that is not found in the genome of the organism from which the tissue sample of interest is obtained, and therefore, is not expected to hybridize to cellular RNA in the tissue sample. In one embodiment, the entirety of an extension consists of a detection sequence; that is, the entirety of the 5-end and 3'-end extensions are unique and not found genome of the organism. The detection sequence may be about 18 to about 30 nucleotides long. Typically, the detection sequence in the 5-end extension is different from the one in the 3'-end extension. The detection sequences may be used for detection, for instance, by hybridizing to the detection sequence a short oligonucleotide, which is complementary to at least about 15 consecutive nucleotides of the detection sequence. The short complementary oligonucleotide comprises a detectable label, such as a fluorescent moiety. Any detectable label known in the art may be used. The detection sequences may also be used as PCR primer sites and/or probe hybridization sites. Preferably the 5'-end and 3'-end extensions do not contain sequence that forms stable hairpin loops. The skilled artisan is familiar with designing oligonucleotides sequences with desired properties. There are numerous publicly available programs that assist in designing oligonucleotides and minimizing such things as undesirable secondary structure, such as hairpins and primer-dimers.

The 5'-end extension and the 3'-end extension optionally may each further comprise a restriction site. The sites may be the same or different in a probe. Preferably, the restriction site is for a class II restriction endonuclease that cuts distal from the sequence-specific part of the cognate recognition site. The preferred type of class II restriction endonucleases have a cognate recognition site that includes $(N)_y\hat{}$ where "y" indicates the number of N residues between the sequence-specific part and the cut site, and the "^" indicates the cut site. One example is Fok I, which recognizes:

$$5'-GGATG\ (N)_9\blacktriangledown-3'$$
$$3'-CCTAC\ (N)_{13}\blacktriangle-3'$$

and cleaves the two strands at the position of the arrowheads, leaving a 4 base 5' overhang. Other examples of endonucleases useful in the invention include, but are not restricted to, Eco 57I, Fal I, Fau I, Gsu I, Hph I, Hin 4I, Mbo II, and Mme I. In one embodiment, both the 5'-end extension and the 3'-end extension comprise a Fok I site. In another preferred embodiment, the restriction site is for a homing endonuclease. Preferably, the homing endonuclease is I-CeuI. This endonuclease has a longer recognition site of about 16 base-pair consensus sequence. The longer site is advantageous in the method of the invention since it is less likely to be found within the sequence tag compared to shorter recognition sites. In another embodiment, both the 5'-end extension and the 3'-end extension comprise an I-CeuI site In a preferred embodiment, when the method includes a subcloning step as discussed elsewhere herein, the restriction sites flank the sequence tag and the detection sequences flank the restriction sites. FIG. 1 is a schematic representation of this embodiment.

The sequence tag, also referred to herein as a "PACES tag," is typically a sequence of about 18 to about 28 nucleotides, and more preferably about 18 to about 22 nucleotides. A sequence of about 18 nucleotides will, statistically speaking, likely be present only once in the human genome. That is, the sequence, if present in the human genome, is unique (probability of any given 18 nucleotide sequence is 1 in about $6\times10^{10}$). The sequence tag is the portion of the oligonucleotide sequence probe that may hybridize to a complementary sequence in a nucleic acid in a tissue sample. The relatively short length of the sequence tag is intended to reflect the short lengths of nucleic acid between points of crosslinking in a fixed tissue sample. For tissue samples wherein the lengths of nucleic acid between cross-linked points are known or expected to be longer, a longer sequence tag is possible.

The sequence tag may comprise a specific sequence, for instance, from a gene of interest. The oligonucleotide probe is thereby targeted to nucleic acids comprising the complement of this sequence. This embodiment is useful, for instance, for probing for the presence and location of a specific gene transcript in a pathological tissue specimen. One may use a single oligonucleotide probe is such applications, or a population of oligonucleotide probes. The population may comprise probes having sequence tags directed to different genes, different regions of the same gene, splice variants of the same gene or combinations thereof. The population may further comprise probes having a sequence tag with a degenerate sequence. These populations are useful, for instance, in methods using gene signatures, such as for a diagnosis or prognosis of cancer, a measure of cancer aggression, or a measure of likelihood of local recurrence or metastatis, methods which typically employ several dozen specific probes.

Alternatively, the sequence tag may comprise degenerate sequence. An oligonucleotide sequence probe with the degenerate sequence 5'-GC(A/G)CTGG-3' probes for two different sequences. The sequence tag may be degenerate at one or more positions. Each degenerate position may comprise one of two, three or four different nucleotides. Preferably, the sequence tag is degenerate at five or more positions, more preferably, 10 or more positions and most preferably still, at all positions. Preferably, each degenerate position comprises 4 different nucleotides. Thus, in the method of the invention, a tissue sample may be probed with a population of oligonucleotide sequence probes wherein there are two or more different sequence tags present in the population. Thus, multiple expressed sequences may be detected simultaneously in a biological sample. When the sequence tag is degenerate at all positions and each position may comprise one of four different nucleotides, a population of oligonucleotide sequence probes having a highly diverse number of sequences in the sequence tag portion of the probe is made. Any single oligonucleotide sequence probe has a sequence tag, which, if present in the genome of the organism of the tissue sample of interest, is expected to be unique.

Figure 2:
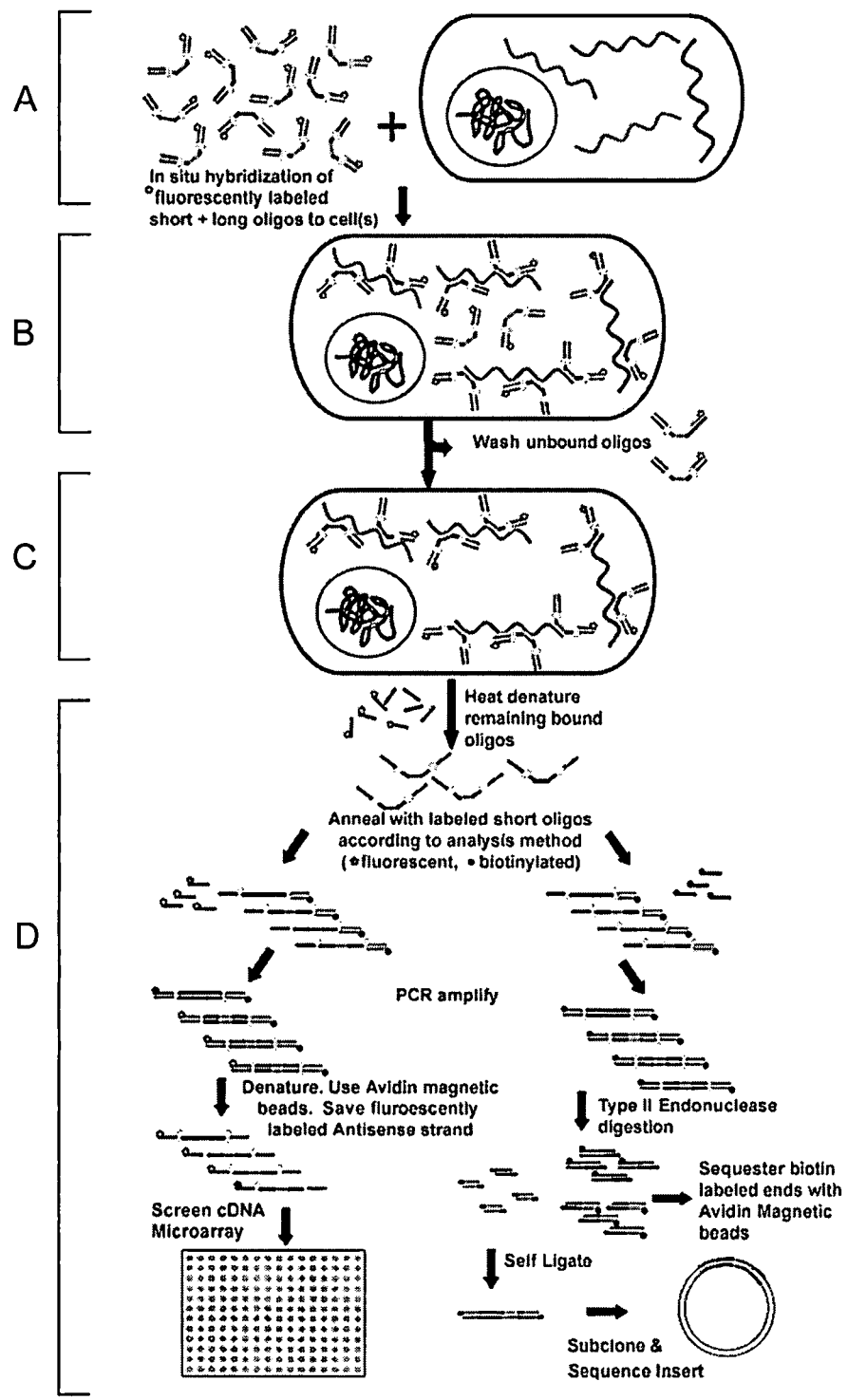
FIG. 2 is a schematic illustration of the method of the invention. The large oval represents a cell containing a nucleus (circle) within which is chromosomal material (black squiggly tangle). The zigzag lines outside of the nucleus represent mRNA. The short bent lines represent oligonucleotide sequence probes. The gray ovals on the short bent lines represent restriction sites. The small lines parallel to the ends of the bent lines represent complementary oligonucleotides. The short lines with a circle represent fluorescently-labeled oligonucleotides. The short lines with black dots represent biotinylated oligonucleotides.

The population of oligonucleotide sequence probes having one or more sequence tag sequences are used in an in situ hybridization step. The oligonucleotide sequence probes optionally bear a detectable label. The label may be covalently attached to the oligonucleotide probe or may be non-covalently attached. For instance, in one embodiment, detection oligonucleotides that bear a detectable label and are complementary to one or both detection sequences, are hybridized to the oligonucleotide sequence probes prior to hybridization with the tissue sample. This embodiment is schematically shown in FIG. 2A, wherein the short lines with circles represent fluorescent-tagged oligonucleotides. Hybridization to nucleic acid in the tissue sample occurs via the sequence tags embedded in the probes, as schematically shown in FIG. 2B. In a preferred embodiment, wherein the sequence tag is degenerate, multiple, different sequence tags are expected to hybridize to any given RNA present in the tissue sample, depending on the sequence of the RNA molecule. This is illustrated in FIG. 2B, for instance, on the far right of the "cell". Increasing the degeneracy in the population of oligonucleotide sequence probes, which increases the diversity of sequences, increases the likelihood of each RNA molecule in the tissue sample hybridizing to at least one sequence tag. When there is a sufficient diversity of sequences, statistically, all cellular RNA should hybridize to multiple oligonucleotide sequence probes having different sequences in their sequence tag portion. See FIG. 2B.

Methods of reducing or eliminating non-specific binding of the oligonucleotide sequence probes are known to the skilled artisan. However, the use of tRNA or ssRNA, which are traditionally used as blockers in in situ hybridization, is not preferred when the oligonucleotide sequence probes comprise a degenerate sequence tag. This is because tRNA or ssRNA will themselves hybridize to some subset of the oligonucleotide sequence probes. In embodiments using an oligonucleotide sequence probe comprising a degenerate sequence tag, non-specific binding may be reduced by adding an excess of a single oligonucleotide sequence probe. For instance, an excess of an oligonucleotide sequence probe having one out of the possible $4^{20}$ sequences in the population of sequences, when the sequence tag comprises 20 degenerate positions, is used to reduce non-specific binding. Any non-specific binding to tissue should be saturated by the excess single PACES oligonucleotide sequence probe, thus allowing the remaining ($4^{20}$–1) sequences in the population of oligonucleotide sequence probes to specifically interact with complementary nucleic acid sequences in the target tissue. In addition, while the oligonucleotide sequence probes may bind to complementary sequences in DNA, such binding is not expected to confound binding to RNA, for several reasons. First, the representation of each sequence tag sequence in the DNA is expected to be low, whereas even low abundance RNA is likely present in many multiple copies. Thus, for a given sequence, the oligonucleotide sequences probe is expected to anneal to many more molecules of RNA than to DNA. Second, the double-stranded nature of DNA will reduce any potential hybridization. Third, the DNA binding proteins will also inhibit potential hybridization to the DNA.

After the hybridization step, the sample is washed in order to remove unhybridized oligonucleotide sequence probes, leaving the population of hybridized oligonucleotide sequence probes (FIGS. 2B and 2C). Hybridization may be monitored by using an imaging agent. For instance, hybridization may be monitored by annealing, for instance, fluorescently-tagged short oligonucleotides, complementary to one or both detection sequence, to the oligonucleotide sequence probes after they are hybridized to a nucleic acid in tissue sample. Alternatively, the detectably-labeled short oligonucleotides are annealed to the oligonucleotide sequence probes prior to the hybridization step, and then are detected to monitor hybridization. Advantageously, detection of fluorescent or other visibly detectable labels permits the identification and dissection of groups of cells, single cells, or subregions of cells, such as dendrites or axons, from which the hybridized oligonucleotide sequences probes may then be isolated for characterization. Advantageously, therefore the method of the invention permits the identification of sequences in specific cells or subregions of cells in a tissue sample.

The population of hybridized oligonucleotide sequence probes may also be isolated for further characterization. Isolation may be done by dehybridizing the oligonucleotide sequence probes from the tissue sample. Dehybridization can be done by any method known to the skilled artisan, including heat denaturation, solutions that denature double-stranded nucleic acid, including, for instance, formamide or sodium hydroxide, and combinations thereof (FIGS. 2C and 2D). The sequence probes may be characterized by any suitable method known in the art or subsequently developed.

The isolated population of oligonucleotide sequence probes may be amplified. Amplification of the isolated oligonucleotide sequence probes may be carried out by any method known to the skilled artisan. See, for instance, Kwoh et al., (1990, Am. Biotechnol. Lab. 8, 14-25) and Hagen-Mann, et al., (1995, Exp. Clin. Endocrinol. Diabetes 103:150-155). Amplification methods include, but are not limited to, polymerase chain reaction ("PCR") including RT-PCR, strand displacement amplification (Walker et al., 1992, PNAS 89, 392-396; Walker et al., 1992, Nucleic Acids Res. 20, 1691-1696), strand displacement amplification using Phi29 DNA polymerase (U.S. Pat. No. 5,001,050), transcription-based amplification (Kwoh et al., 1989, PNAS 86, 1173-1177), self-sustained sequence replication ("3SR") (Guatelli et al., 1990, PNAS 87, 1874-1878; Mueller et al., 1997, Histochem. Cell Biol. 108:431-437), the Q.beta. replicase system (Lizardi et al., 1988, BioTechnology 6, 1197-1202; Cahill et al., 1991, Clin., Chem. 37:1482-1485), nucleic acid sequence-based amplification ("NASBA") (Lewis, 1992, Genetic Engineering News 12 (9), 1), the repair chain reaction ("RCR") (Lewis, 1992, supra), and boomerang DNA amplification (or "BDA") (Lewis, 1992, supra). PCR is the preferred method of amplifying the target polynucleotide sequence.

PCR may be carried out in accordance with known techniques. See, e.g., Bartlett et al., eds., 2003, PCR Protocols Second Edition, Humana Press, Totowa, N.J. and U.S. Pat. Nos. 4,683,195; 4,683,202; 4,800,159; and 4,965,188. In general, PCR involves, first, treating a nucleic acid sample (e.g., in the presence of a heat stable DNA polymerase) with a pair of amplification primers. One primer of the pair hybridizes to one strand of a target polynucleotide sequence. The second primer of the pair hybridizes to the other, complementary strand of the target polynucleotide sequence. In the instant invention, the first cycle of PCR produces the complementary strand of the oligonucleotide sequence probes. The primers are hybridized to their target polynucleotide sequence strands under conditions such that an extension product of each primer is synthesized which is complementary to each nucleic acid strand. The extension product synthesized from each primer, when it is separated from its complement, can serve as a template for synthesis of the extension product of the other primer. After primer extension, the sample is treated to denaturing conditions to separate the primer extension products from their templates. These steps are cyclically repeated until the desired degree of amplification is obtained.

The primers for PCR amplification may anneal to any sequence in the 5'-end and 3'-end extensions of the oligonucleotide sequence probe. In one embodiment, the primers anneal to the detection sequences. The primers used in the PCR may be tagged, for instance, with biotin or a detectable label, such as a fluorescent moiety, using any method known in the art. For instance, primers may include aminoallyl-substituted nucleotides at one or more positions, enabling subsequent fluorescent labeling. Primers may contain two or more such labels, such as two different types of fluorophores. These tags may subsequently be used to isolate and detect efficiently the resulting amplified DNA fragments (also referred to herein as amplicons). In an embodiment in which one primer is biotinylated and the other primer has a detectable label (see left side of FIG. 2D), the amplified detectably-labeled strand may be readily separated from the amplified biotinylated complementary strand using, for instance, an affinity resin comprising avidin. The sequences present in the sequence tags of the detectably-labeled strands may then be characterized, for instance, by hybridization to a cDNA microarray (FIG. 2D, left side). Other arrays useful in the method of the invention include, but are not limited to, 500K arrays (Affymetrix) and gene signature arrays. Abundance of each particular sequence in the population of sequence tags may also be quantified using standard techniques, for instance, quantitative detection of the fluorescent label intensity.

Alternatively, the amplicons may be directly sequenced using methods known to the skilled artisan. A variety of automated sequencing procedures may be utilized, including sequencing by mass spectrometry (see, e.g., PCT International Publication No. WO 94/16101; Cohen et al., 1996, Adv. Chromatogr. 36:127-162; and Griffin et al., 1993, Appl. Biochem. Biotechnol. 38:147-159) and pyrosequencing. Traditional sequencing methods may also be used, such as dideoxy-mediated chain termination method (Sanger et al., 1975, J. Mol. Biol. 94: 441; Prober et al. 1987, Science 238: 336-340) and the chemical degradation method (Maxam et al., 1977, PNAS 74: 560).

In a preferred embodiment, the amplicons are cloned into an appropriate vector prior to sequencing. If the oligonucleotide sequence probes are designed as illustrated in FIG. 1, the amplicons comprise the restriction sites in the 5'-end and 3'-end extensions. The amplicons may, therefore, be restriction-enzyme digested and subcloned into a vector (FIG. 2D, right side). Preferably, the digested amplicons are ligated together to form concatamers prior to subcloning into a vector. The skilled artisan is familiar with designing an oligonucleotide sequence and choosing restriction enzyme sites to enable self-ligation of products from a restriction digest. The skilled artisan is also familiar with ways to limit self-ligation such that only two digested amplicons will ligate, or to produce multiple amplicons ligated together. In some instances, a concatamer with multiple amplicons ligated together may be treated with a restriction enzyme to enrich for a particular-sized concatamer, which is then subcloned into a vector. Any cloning vector may be used in the method of the invention. Similarly, any suitable host cell for propagating the cloning vector may be used. Vectors and host cells are well known to the skilled artisan.

After subcloning and sequencing, the sequence tag sequences in a concatamer may be readily distinguished from non-sequence tag sequences because the non-sequence tag sequences are identical in all the amplicons. The frequency with which a given sequence is identified in the sequenced sequence tags reflects the abundance of the cellular RNA containing that sequence in the biological sample.

Once the sequences of the sequence tags are determined by microarray hybridization, by sequencing chemically the sequence tags or any other suitable method of sequence characterization, they may be compared to sequences in public databases to identify the genes. Thus, despite the short pieces of RNA typically found in fixed pathological tissue samples, the method enables gene expression profiling. Advantageously, a single RNA sequence in a biological sample is expected to hybridize to multiple sequence tags with different sequences, there should be multiple sequences identified for each RNA sequence and thus, multiple measures of abundance. While these measures of abundance are not independent, and will likely be influenced by the hybridized sequence and the stringency of the hybridization, dramatically different measures of abundance might be informative. For instance, for a gene for which two different sequence tags are identified, if the abundance of one sequence tag is much less than the other, this might reflect a truncation or other variant of the gene is present in the biological sample.

The inventive procedure works on fixed tissue because of the small region of RNA to which the oligonucleotide sequence probe hybridizes. Even if a particular region of a particular RNA is degraded or otherwise unable to hybridize, other regions of that RNA should still be available for hybridization. The in situ hybridization is temperature and salt concentration sensitive and these parameters can be manipulated readily by the skilled artisan to facilitate isolation and cloning of different subpopulations of RNA. Advantageously, the PCR reaction is over such a short distance that PCR skewing, a well-known artifact, is minimized in the method of the invention.

Any tissue sample from a subject may be used in the method of the invention. Examples of tissue that may be used include, but are not limited to, breast, prostate, ovary, colon, lung, endometrium, stomach, salivary gland and pancreas. The tissue sample can be obtained by a variety of procedures including, but not limited to surgical excision, aspiration or biopsy. The tissue may be embedded in paraffin or frozen.

In one embodiment, the tissue sample is fixed. The tissue sample may be fixed (i.e. preserved) by any conventional methodology. See e.g., "Manual of Histological Staining Method of the Armed Forces Institute of Pathology," 3rd edition (1960) Lee G. Luna, HT (ASCP) Editor, The Blakston Division McGraw-Hill Book Company, New York; The Armed Forces Institute of Pathology Advanced Laboratory Methods in Histology and Pathology (1994) Ulreka V. Mikel, Editor, Armed Forces Institute of Pathology, American Registry of Pathology, Washington, D.C. One of skill in the art will appreciate that the choice of a fixative may be determined by the purpose for which the tissue is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a tissue sample.

Generally, the tissue sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology See e.g., "Manual of Histological Staining Method of the Armed Forces Institute of Pathology", supra. Examples of paraffin that may be used include, but are not limited to, PARAPLAST®, Broloid, and Tissuemay. Once the tissue sample is embedded, the sample may be sectioned by a microtome or the like. See e.g., "Manual of Histological Staining Method of the Armed Forces Institute of Pathology", supra. By way of example for this procedure, sections may range from about three microns to about five microns in thickness. Once sectioned, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine.

The selection of a specific fixation protocol will be dictated by several factors. First, the fluorescent probe to be used may place restrictions on which treatment may be necessary (i.e. some fixations prevent binding of certain dyes). Second, the size or thickness of a given sample may preclude the use of certain fixatives due to permeability (i.e. a fixative that is unable to penetrate into thick samples will only preserve the outer layers).

Fixation by cross-linking is a method commonly used for fluorescence microscopy. It involves treating specimens with reagents that penetrate into the cells and tissues and form covalent cross-links between intracellular components. The most commonly used cross-linking agents are aldehydes, which form covalent bonds between adjacent amine-containing groups through Schiff acid-base reaction. These bonds form both inter- and intra-molecularly and are, therefore, very effective fixatives for proteins and nucleic acids. The two most frequently used aldehydes are formaldehyde and glutaraldehyde. Both fixatives have advantages and disadvantages, which will be discussed below. Other aldehydes, such as acrolein, have been used historically, but do not preserve samples as well.

Glutaraldehyde is a four carbon molecule terminated at both ends by aldehyde groups. It is an extremely efficient fixative, and is widely used in light and electron microscopy because of its efficacy in preserving cellular structure. In some instances, however, other fixatives may be preferred. For instance, the comparatively high molecular weight of glutaraldehyde limits its ability to diffuse into thick specimens, such as tissue sections or embryos. In addition, as a tissue is cross-linked by the fixative, glutaraldehyde's ability to penetrate over time diminishes. For such samples, formaldehyde may be a better option. Second, free aldehyde groups fluoresce efficiently at the same wavelengths as many of the fluorescent probes employed by biologists. As glutaraldehyde possesses two functional groups per molecule, background autofluorescence may be a significant problem in fixed tissues, effectively lowering the probe's signal to noise. This problem may be circumvented by using relatively low concentrations of glutaraldehyde (i.e. less than 1%). Unreacted aldehydes may also be quenched by treating fixed samples with reducing agents, such as sodium borohydride, to reduce free aldehyde groups to alcohols, or by reacting them with exogenous amine-containing reagents, such as ammonium chloride or glycine. In a preferred embodiment of the present invention, the fixed tissue is treated with sodium borohydride to quench autofluorescence.

Formaldehyde is probably the most commonly used cross-linking fixative for biological samples. It has a single aldehyde-containing carbon and exists as a gas. Formaldehyde does not cross-link as effectively as glutaraldehyde, and for this reason is rarely used by-itself for electron microscopy. However, its small molecular weight allows it to penetrate cells and tissues rapidly, making it a choice fixative for thicker samples and autofluorescence of unreacted aldehyde groups is not usually a problem.

If so desired, the tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De® (CMS, Houston, Tex.) may be used. Advantageously, however, the method of the invention does not require deparaffinization. Thus, archival samples are preserved when subjected to the method of the invention, and may conceivably be re-used.

Various degrees of hybridization stringency can be employed. As the hybridization conditions become more stringent, a greater degree of complementarity is required between the probe and target to form and maintain a stable duplex. Stringency is increased by raising temperature, lowering salt concentration, or raising formamide concentration. Adding dextran sulfate or raising its concentration may also increase the effective concentration of labeled probe to increase the rate of hybridization and ultimate signal intensity. After hybridization, slides are washed in a solution generally containing reagents similar to those found in the hybridization solution with washing time varying from minutes to hours depending on required stringency. Longer or more stringent washes typically lower nonspecific background but run the risk of decreasing overall sensitivity.

The degree of homology required for stable hybridization varies with the stringency of the hybridization medium and/or wash medium. Preferably, completely homologous probes are employed in the present invention, but persons of skill in the art will readily appreciate that probes exhibiting lesser but sufficient homology can be used in the present invention [see for e.g. Sambrook, J., Fritsch, E. F., Maniatis, T., Molecular Cloning A Laboratory Manual, Cold Spring Harbor Press, (1989)]. As used herein, stringency of hybridization may be determined as follows or using other protocols known to one of skill in the art:

1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

It is understood that equivalent stringencies may be achieved using alternative buffers, salts and temperatures.

Hybridization of the oligonucleotide sequence probes may be varied, since the tissue of interest will have RNAs of varying GC sequence content. Hybridization temperature and washing stringencies that favor binding of GC-rich sequences may be different from those that favor binding of AT-rich sequences. In some instances, a series of temperature and washing stringencies may be required to capture sequence tags at each GC extreme.

It is expected that the PACES oligonucleotide sequence probe will bind to rRNA and tRNA, in addition to mRNA. If the subcloning and direct sequencing embodiment of the invention is used, an overwhelming number of sequence tags identified will likely correspond to rRNA and/or tRNA, and not to mRNA. Therefore, for the subcloning and direct sequencing embodiment, a subtraction step is desirable. By way of example, prior to subcloning and sequencing, the PCR-amplified amplicons are hybridized to biotinylated rRNAs and tRNAs. The biotinylated complexes are then selectively removed from the population of amplicons using, for instance, an avidin or streptavidin affinity resin. Notably, however, rRNA and tRNA should not affect the cDNA microarray analysis embodiment. Addressable arrays allow tRNA and/or rRNA signals to be identified and thus, should not confound the analysis.

Probes are preferably labeled with a fluorophore. Examples of fluorophores include, but are not limited to, rare earth chelates (europium chelates), Texas Red, rhodamine, fluorescein, dansyl, phycocrytherin, phycocyanin, spectrum orange, spectrum green, and/or derivatives of any one or more of the above. Multiple probes used in the assay may be labeled with more than one distinguishable fluorescent or pigment color. These color differences provide a means to identify, for example, the hybridization positions of specific probes. Moreover, probes that are not separated spatially can be identified by a different color light or pigment resulting from mixing two other colors (e.g., light red+green=yellow) pigment (e.g., blue+yellow=green) or by using a filter set that passes only one color at a time.

Probes can be labeled directly or indirectly with the fluorophore, utilizing conventional methodology. Indirect labeling includes the use of dendritic nucleic acids. Additional probes and colors may be added to refine and extend this general procedure to serve as internal controls.

There are three main ways in which cells and tissues may be processed to retain their structural organization for subsequent experimentation. These are fixation by cross-linking, fixation by precipitation, and fixation by freezing (cryofixation). Cryofixation, is probably the best technique for cellular preservation, and is often employed for electron microscopy for this reason. It involves rapidly freezing the cells or tissues on a cooled block of heat-conductive metal or rapid plunging into a cold medium, such as liquid nitrogen or freon. Following freezing, the samples may then be treated with a cross-linking reagent, discussed below, in a process called "freeze substitution". The disadvantages of cryofixation are that it typically requires specialized equipment usually unavailable in most laboratories.

Methods for detecting a target nucleic acid fragment directly from a specimen are comprised of multiple steps which are typically performed in the following order. A specimen, usually obtained from a patient, is fixed and embedded in paraffin. The embedded tissue may be sectioned. The sample is treated in keeping with the inventive method. The nucleic acids of the sample are then incubated with labeled oligonucleotide sequence probes, under conditions appropriate for hybridization.

The quantity of the total probe used is a predetermined amount which should exceed the estimated amount of the available target believed to be within the sample (about 100:1) in order to drive the hybridization reaction efficiently and to promote a high rate of probe:target annealing. The labeled probe is incubated with the nucleic acids of the fixed sample. In one embodiment, the labeled probe is generally added in solution onto the sample. Conditions appropriate for hybridization are solutions which provide the appropriate buffered environment. The specific concentration of hybridization buffer varies with the nucleic acid sequence and length of the probe. The exact concentration of buffer used is dependent on the $T_m$ of the probe, probe sequence, probe length, and hybridization temperature, and may be readily determined by one of skill in the art through the course of no more than routine experimentation.

After hybridization is complete, the non-hybridized oligonucleotide sequence probes are typically rinsed from the sample, generally by applying a series of stringent washes with a wash buffer. It is within the means of those skilled in the art to determine appropriate wash buffers. In one embodiment, the wash buffer is 0.3 M sodium chloride, 0.03 M sodium citrate, and 0.5% NP40. In another embodiment, the wash buffer is phosphate buffered saline (PBS). In a further embodiment, the wash is formamide/sodium citrate.

In one embodiment, any detectably-labeled short oligonucleotide probe that is hybridized to the nucleic acid of the fixed sample is then visually detected by microscopy. The presence of detectably-labeled probe within the sample is an indication of the presence of the target nucleic acid fragment, if the sequence tag is directed to a set of sequences. The sensitivity of this method has been determined to detect as few as 10 copies of target nucleic acid.

It should be appreciated that the use of formamide or GuSCN in the hybridization fluid allows hybridization to be carried out at a much lower temperature than standard hybridization protocols. Hybridization of an average probe specifically to a target (and not to host cells) in aqueous hybridization fluid such as sodium chloride would generally require a temperature of 60-65° C. The same hybridization performed at 42° C. in hybridization buffer described above, would provide specificity.

The population of hybridized oligonucleotide sequence probe is detected by means suitable for the specific moiety used to label the probe. In one embodiment, the marker moiety is a fluorophore. In a preferred embodiment, the fluorophore is FITC, Fluo-3,5 hexadecanoyl fluorescein, Cy2, fluorX, Cy3, Cy3.5, Cy5, Cy5.5, Cy7, fluorescein and Texas Red. For example, the preferred method for detecting a fluorescent-labeled probe employs special filters such as a blue filter (fluorescent labeled probe) and a green filter (for rhodamine-X or Texas red labeled probe).

Advantageously, the method of this invention may be used for simultaneous detection of multiple different transcripts in a single clinical sample by performing one reaction with a population of oligonucleotide sequence probes, which population is comprised of a plurality of different sequence tags. In one embodiment, each different sequence tag is labeled with a different marker moiety. For simultaneous detection, the sequence tags that are specific for the different nucleic acids commonly present in a clinical specimen can be designed such that the $T_m$ values of all the sequence tags are very similar. Each specific oligonucleotide sequence probe is then labeled with a different detectable moiety (e.g. different fluorescent moieties). Hybridization is performed with the multiple oligonucleotide sequence probes. The hybridized sample is processed as described above and hybridization is observed by means appropriate for detection of the different labeled probes (e.g. viewed using appropriate filters if different fluorescent moieties are used) to detect which transcripts are detected in the sample.

The method of the invention may be used to identify a truncated mRNA. A population of oligonucleotide sequence probes comprising a degenerate sequence tag is hybridized to a biological specimen, non-hybridized probes are removed by washing, and the population of hybridized oligonucleotide sequence probes is isolated. The isolated population is then characterized to assess the relative amount of the two different regions of the same gene. Such characterization may be accomplished, for instance, by amplifying the isolated population and hybridizing it to a microarray that is capable of detecting sequences for the two different regions of at least one mRNA. The population of oligonucleotide sequence probes is detectably labeled, as described elsewhere herein, either before or after the hybridization step. The detectable label is then detected and the strength of the signal from the two regions of the mRNA is compared. A difference in signal strength or the absence of one signal and not the other is indicative of a truncation in the mRNA. The method may also use oligonucleotide sequence probes comprising sequence tags that are targeted to a specific gene or genes, to test for truncation in a specific gene known or suspected of being truncated.

It will be recognized by practitioners ordinarily skilled in this art that the novel in situ hybridization protocol described herein is compatible with all previously known methods of detection as well as the one described herein. The reagents described in the present invention may be provided in a kit form to practice the method, which has been optimized for simplicity and for compatibility with a wide variety of detection methods. Such prepared kits may further contain specifically-prepared reagents and probes, and will be applicable in clinical/diagnostic laboratories, where the ability to detect the presence or absence of specific nucleic acids would serve to positively or negatively identify pathological states characterized by the presence of specific genes. In a preferred embodiment, such methods are designed for use with fixed treated tissue and would comprise reagents necessary therefore.

In one embodiment, the invention provides a kit for identifying a nucleic acid from a biological specimen. The kit comprises an oligonucleotide sequence probe that comprises, in order 5' to 3', a first sequence element comprising a sequence of about 18 to about 22 nucleotides that is not found in the human genome, a second sequence element that is a degenerate sequence and is about 18 to about 28 nucleotides long, and a third sequence element that comprises a sequence of about 18 to about 22 nucleotides that is not found in the human genome and wherein said first sequence element and said third sequence elements are different from each other and wherein said oligonucleotide sequence probe is about 72 to about 150 nucleotides long. The kit further comprises a first primer and a second primer. The first primer consists of a sequence that is identical to at least about 15 consecutive nucleotides of the first sequence element and the second primer consists of a sequence that is 100% complementary to at least about 15 consecutive nucleotides of the third sequence element. The kit further comprises an instructional material.

In one embodiment, the oligonucleotide sequence probe in the kit further comprises a fourth sequence element of about 18 to about 30 nucleotides, positioned between the first and second sequence elements, and comprises a first restriction site, and a fifth sequence element of about 18 to about 30 nucleotides, positioned between the second and third sequence elements and comprises a second restriction site. In another embodiment, the first and second restriction sites are Fok I sites.

The invention also provides a kit useful for targeting a nucleic acid from a biological specimen. The kit comprises an oligonucleotide sequence probe that comprises, in order 5' to 3', a first sequence element comprising a sequence of about 18 to about 22 nucleotides that is not found in the human genome, a second sequence element that is a sequence in a targeted nucleic acid and is about 18 to about 28 nucleotides long, and a third sequence element that comprises a sequence of about 18 to about 22 nucleotides that is not found in the human genome and wherein said first sequence element and said third sequence elements are different from each other and wherein said oligonucleotide sequence probe is about 72 to about 150 nucleotides long. In some embodiments, the kit comprises a population of oligonucleotide probes wherein there are two or more different sequences to a targeted nucleic acid present as the second sequence element. As discussed elsewhere herein, the two or more different sequences may target the same gene, splice variants of the same gene, different regions of the same gene variants of the same gene or may target different genes. The kit further comprises a first primer and a second primer. The first primer consists of a sequence that is identical to at least about 15 consecutive nucleotides of the first sequence element and the second primer consists of a sequence that is 100% complementary to at least about 15 consecutive nucleotides of the third sequence element. The kit further comprises an instructional material.

In another embodiment, at least one of the primers comprises biotin or a detectable label. In another embodiment, one primer comprises biotin and the other primer comprises a detectable label. In another embodiment, the detectable label is selected from the group consisting of a chromogenic moiety, a radioactive moiety and a fluorescent moiety.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Hybridization of Population of Oligonucleotide Sequence Probes Comprising Degenerate Sequence Tags to Fixed Sample A 100 base pair oligonucleotide sequence probe was synthesized by a commercial vendor (Sigma-Genosys). The oligonucleotide sequence probe comprised a 20 base pair degenerate sequence as its sequence tag, located approximately in the middle of the probe and flanked by 5'-end and 3' end extension sequences, arranged as depicted in FIG. 1. A BLAST search confirmed that the 5'-end and 3'-end extension sequences flanking the sequence tag are not found in the mammalian genome. Each extension sequence comprised a FokI site.

Figure 3:
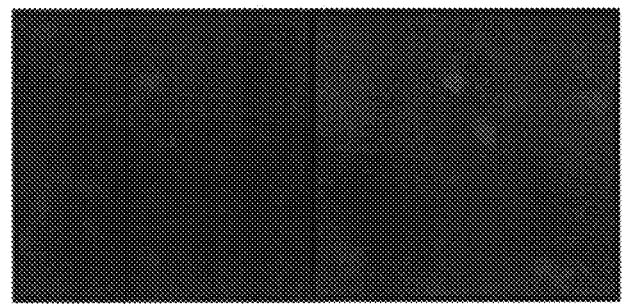
FIG. 3 depicts primary cortical neurons visualized during in situ hybridization with a fluorescently-labeled short oligonucleotide complementary to a detection sequence in the oligonucleotide sequence probe, as described in Example 1. The left panel is a depiction in the absence of the oligonucleotide sequence probe (establishing background fluorescence signal). The right panel is a depiction in the presence of the oligonucleotide sequence probe.

Two short, fluorescently-labeled oligonucleotides, complementary to detection sequences at the ends of the oligonucleotide sequence probe, were hybridized to the oligonucleotide sequence probe. The population of oligonucleotide sequence probes, each having double-stranded ends and a single-stranded middle section comprising the degenerate sequence tag, was hybridized in situ to primary cortical neurons, fixed with 4% paraformaldehyde. As a control, the two short, fluorescently-labeled oligonucleotides were also hybridized to primary cortical neurons in the absence of the oligonucleotide sequence probe. As depicted in FIG. 3, neurons subjected to in situ hybridization with the oligonucleotide sequence probe were clearly visualized using the fluorescent short oligonucleotides.

After hybridization, a series of washing steps of increasing stringency effectively removed oligonucleotide sequence probes that were not hybridized. The population of hybridized oligonucleotide sequence probes was eluted using deionized water.

Figure 4:
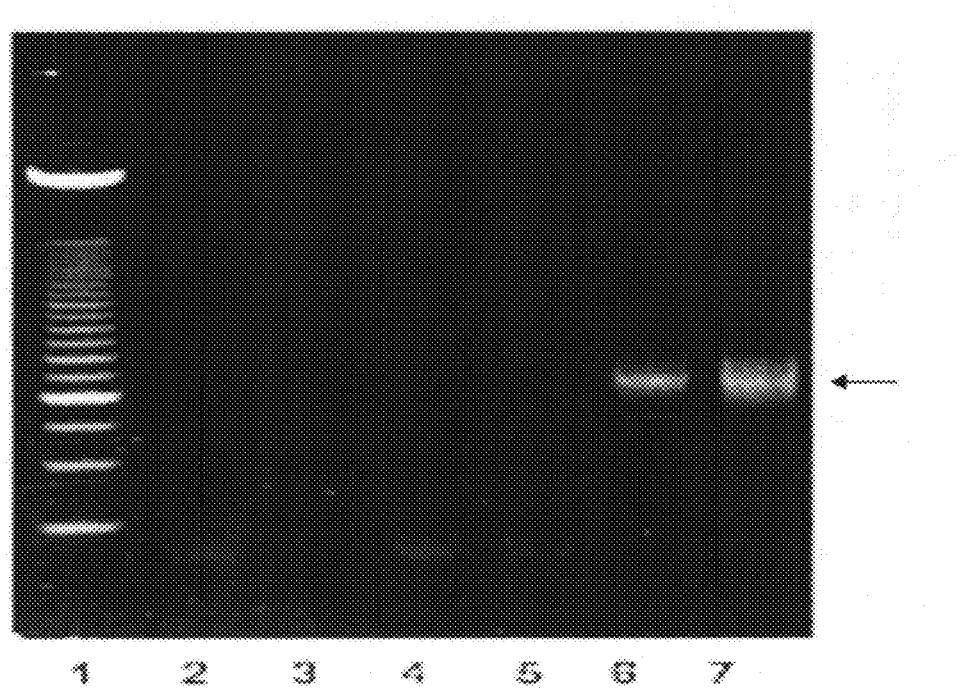
FIG. 4 depicts an image of a non-denaturing DNA gel comprising PCR products from PACES performed with primary cortical neuron samples (see Example 1). Lane 1 is a 25 base pair molecular weight ladder. Lanes 2-7 contain the products of PCR amplification using PCR primers complementary to the detection sequences in the oligonucleotide sequence probe. Material recovered from the last washing step prior to elution of the hybridized oligonucleotide sequence probes was used as the PCR template in lanes 2 and 3. The PCR template in lanes 4 and 5 was material recovered from negative controls (in situ hybridization with a primer to a detection sequence but no oligonucleotide sequence probe). The PCR reaction in lane 5 had about twice the amount of the template as the PCR reaction in lane 4. Hybridized oligonucleotide sequence probes recovered from cortical neurons by water elution were used as the PCR template in lanes 6 and 7. The PCR reaction in lane 7 had about twice the amount of template as the PCR reaction in lane 6.

The eluted probes were PCR amplified using the short oligonucleotides complementary to the detection sequences as primers. One probe was fluorescently labelled and the other was biotinylated. FIG. 4 depicts the results of this experiment. A PCR product of the expected length (100 nucleotides) was generated only when the PCR template material was the eluted oligonucleotide sequence probes that hybridized to the cortical cells (lanes 6 and 7). These data demonstrate that the oligonucleotide sequence probes can hybridize to nucleic acids in biological samples and that the hybridized probes can readily be eluted and amplified.

Example 2

Amplification, Subcloning and Sequencing of Hybridized Oligonucleotide Sequence Probes The PACES procedure allows for at least two modes of characterizing the oligonucleotide sequence probes hybridized to nucleic acids in cells: 1) direct hybridization of eluted oligonucleotide sequence probes to a cDNA microarray and 2) a sequencing strategy in which the sequence tags are released from the population of hybridized oligonucleotide sequence probes by digestion with a type II restriction endonuclease and subcloning the released fragments. This example is drawn to the latter mode of characterization.

A 100 base pair oligonucleotide sequence probe having a 20 nucleotide degenerate sequence tag was synthesized. The probe comprised a Fok I site in each end extension sequence. The probe was designed such that when digested with Fok I, a 28 base pair fragment would be released in which the 20 base pair sequence tag was flanked by 6 base pairs upstream (5') and 2 base pairs downstream (3'). See, for instance, Tag #1 in FIG. 5. This design provided sequence tags with known polarity and also permitted concatamerization of the 28 base pair fragments. In addition, no two probes differed in sequence from each other by more than 20 nucleotides, which thus reduces sequence skewing problems.

The oligonucleotide sequence probe was PCR amplified using primers corresponding to sequences in the 5' and 3' end of the oligonucleotide sequence probe. The resulting PCR amplicon was then Fok I digested to release the 28 base pair fragment, (Preliminary experiments using amplicons having a Fok I site in the 5'-end extension and a BtgZ 1 site in the 3'-end extension, or BtgZ 1 sites in both extensions revealed that, while BtgZ 1 did cleave its sites, it was not sufficiently faithful in its cleavage activity. While BtgZ 1 can be used in the method of the invention, it is not preferred.) The fragments were concatamerized, enriched by gel electrophoresis for the size of two sequence tags ligated together ("di-tag"), and subcloned into a Xho I site in pBLUESCRIPT II™. See FIG. 5. Clones were then sequenced using dideoxy-mediated chain termination.

Figures 5, 6:
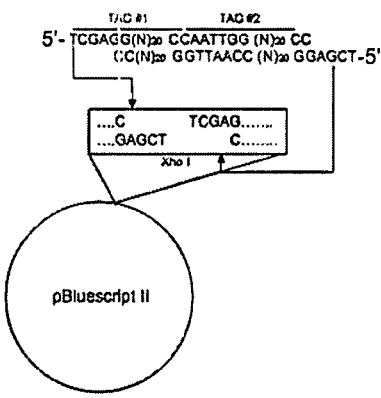
Fig. 5 is a schematic representation of a restriction enzyme digested di-tag and its insertion into a Xho I site of a cloning vector. The two strands are SEQ ID No. 1. Following digestion with FokI, a 28 by fragment including the sequence tag (also called the PACES tag) is released from the oligonucleotide sequence probe. After concatamerization to create di-tags, the di-tags are subcloned into a sequencing vector, pBLUESCRIPT II™, with the appropriate complementary ends.
FIG. 6 depicts the sequence (5' to 3') of five representative di-tags. In each di-tag, the two sequence tags are underlined. The five sequences are, from top to bottom, SEQ ID NOs: 2, 3, 4, 5 and 6.

FIG. 6 shows the sequences of five representative di-tag clones from the experiment that were sequenced. The underlined sequences are the sequence tags. Notably, this representative sample of di-tags had varying GC content. Note that in these experiments, the oligonucleotide sequence probe was not hybridized to cells, but rather, a starting population of oligonucleotide sequence probes was used to test efficiency of various type II restriction enzyme digestions and ligations. Consequently, no Genbank searches were run to identify the genes to which the recovered tags correspond.

Example 3

Microarray

The materials and methods for example 3 are now described.

A 96-base oligonucleotide sequence probe, PACES Long4 oligo (SEQ ID No. 7), containing a 20-base degenerate sequence tag flanked by Fok I restriction sites, was synthesized (Sigma-Genosys). The 20-base degenerate sequence tag corresponds to about $1.1 \times 10^{12}$ different sequences. A probe containing one of these $1.1 \times 10^{12}$ sequences (SEQ ID No. 8; 5'-ACAAATCTCCGTTGTACTGGATGCAT TACG-TAAATTGGAAGTAGTGCGGCACGTCCGGCCTCGAT-TAGTAGAACATCC GGCATTACGTATTTTACC-3') was used to block non-specific binding in the fixed tissue sample. The underlined sequence corresponds to the sequence tag.

Primary cortical cells grown on coverslips were fixed with 4% paraformaldehyde for 15 minutes at 37° C. and then washed twice with 1×PBS (pH=7.4). The fixed cells were subjected to the following incubations, respectively: 0.2% glycine in 1×PBS (5 minutes, twice); 1×PBS (5 minutes, twice); 0.1 M triethanolamine with 0.25% acetic anhydride (10 minutes); 1×PBS (5 minutes, twice); 0.5% Triton-X100 in 1×PBS (15 minutes); and 1×PBS (5 minutes, twice).

Pre-hybridization solution was prepared with the final concentration of 1×SDS-based hybridization buffer (Genisphere, Hatfield, Pa.) and 36 ng/µl single-stranded 96-base SEQ ID No. 8. Cells were pre-hybridized at 42° C. for 1 hour.

In situ hybridization was performed at 42° C. overnight (~16 hours) in 1×SDS-based hybridization buffer (Genisphere) containing 15 ng/µl PACES Long4 oligo (SEQ ID No. 7). The following day, the cells were washed for 15 minutes in prewarmed (42° C.) 2×SSC+0.2% SDS solution, followed by a 10 minute wash in 2×SSC, and a 10 minute wash in 0.2×SSC at room temperature. The population of hybridized oligonucleotide sequence probes was eluted by pipetting 40 µl of hot (85° C.), nuclease-free water onto the coverslip and collecting the solution from the coverslip.

PCR was performed in a 100 µl reaction, using 10 µl eluted solution of the hybridized DNA as template. The population of oligonucleotide sequence probes was amplified with a pair of labeled primers. The 5-PACES PCR primer (SEQ ID No. 9: 5'-ACAAATCTCCGTTGTACTGGAT-3') was fluorescently labeled at the 5' end with Cy3. The 3-PACES PCR primer (SEQ ID No. 10; 5'-GTAAAATACGTAA TGCCGGATG-3') had a biotin at the 5' end.

To increase the yield, 50 mM KCl was added to the PCR reaction. The program was set for a 20-cycle amplification with annealing temperature at 47° C. The PCR products were cleaned up using Microcon-30 (Millipore, Billerica, Mass.) and quantitated by measuring $OD_{260}$.

Mouse 15K cDNA glass arrays were pretreated according to the instruction manual for UltraGAPS™ Coated Slides (Corning Inc. Life Sciences, Acton, Mass.). The mouse 15K cDNA clone set was originally prepared by researchers at the National Institute on Aging (NIA) and is widely distributed. Hybridization was performed at 42° C. over night (~16 hours) in 1×SDS-based hybridization buffer (Genisphere) containing 120 ng/µl PCR-amplified in situ hybridization eluted products. Although the double-stranded PCR product had a biotinylated strand, it was not removed by biotin affinity. Rather, the hybridization mix was denatured at 90° C. for 10 minutes immediately prior to application on the cDNA array. A total of about 600 ng of PCR product was applied to the microarray.

Subsequent work indicated that removing the biotinylated strand from the PCR product dramatically boosted signal on the array. In that work, the biotinylated PCR product was denatured at 90° C. for 10 minutes, and then incubated with Streptavidin beads (Promega) on ice for 1 hour. The supernatant, containing the non-biotinylated amplified strand, was collected and applied to the microarray. As a result, it is expected that the process may be optimized to use fewer PCR amplification rounds and to permit less material to be loaded on the array.

After hybridization, the arrays were washed in 2×SSC+ 0.2% SDS prewarmed at 42° C. for 15 minutes, and followed by a 10 minute wash in 2×SSC and a 10 minute wash in 0.2×SSC, each at room temperature. Slides were scanned for analysis after spin drying.

The results of example 3 are now described.

Figure 7:
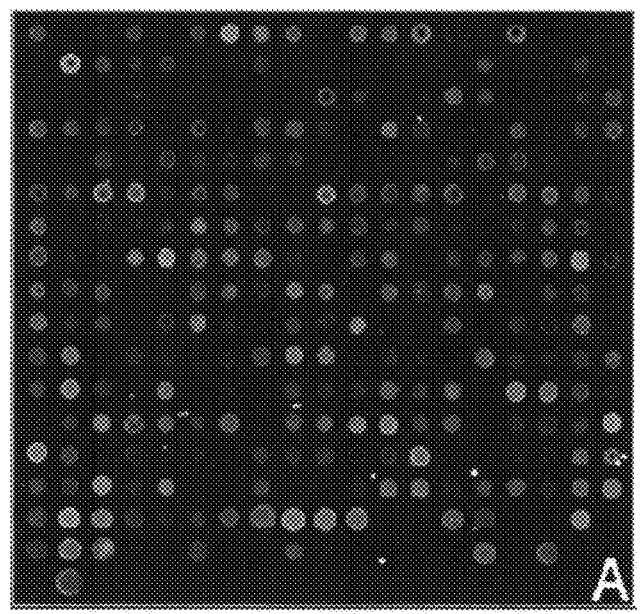
FIG. 7, comprising
Figure 7:
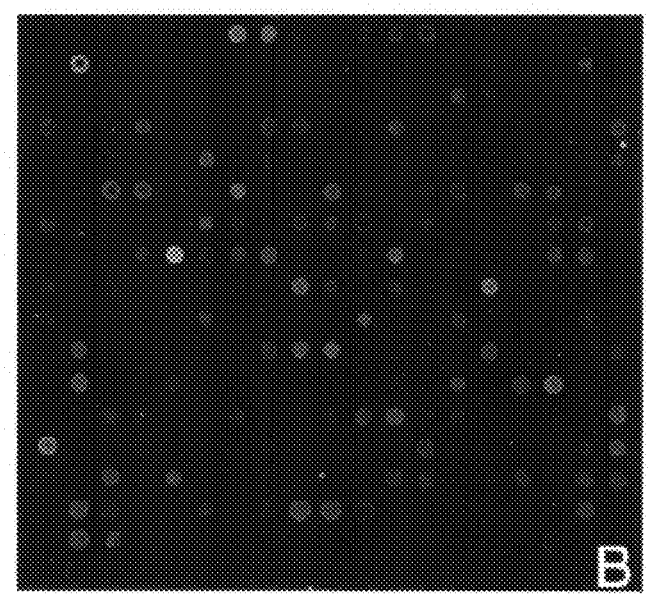

In one experiment, 600 ng of PCR-amplified PACES long oligo that had not been hybridized in situ to the cortical cells was applied to the array. As expected, given the about $1.1 \times 10^{12}$ different sequences present in the sequence tags, most elements on the NIA 15k cDNA array lit up. FIG. 7A depicts the fluorescence pattern of a small portion of this control array.

In another experiment, 600 ng of PCR-amplified PACES long oligo that had been hybridized in situ to cortical cells, eluted and amplified was applied to the array. Overall the fluorescence intensity of this array was diminished compared to the control array, and very few elements on the NIAA 15k cDNA array lit up. See FIG. 7B. Notably, there were a several specific spots that had about equal intensity on both arrays. This result suggests that the corresponding cDNAs are abundantly expressed in the cortical cells to which the population of oligonucleotide sequence probes was hybridized.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of cloning a nucleic acid from a biological sample, wherein said biological sample is fixed, said method comprising:
(a) providing a population of oligonucleotide sequence probes to said fixed biological sample, wherein each of said oligonucleotide sequence probes comprises a sequence tag flanked by a 5'-end extension sequence and a 3'-end extension sequence, wherein said 5'-end and 3'-end extension sequences are not found in the mammalian genome, further wherein said sequence tag is a degenerate sequence and wherein at least one of said 5'-end extension sequence and said 3'-end extension sequence comprises a detection sequence;
(b) hybridizing said population of oligonucleotide sequence probes with said nucleic acid in said biological sample, thereby forming a population of hybridized oligonucleotide sequences probes and a population of unhybridized oligonucleotide sequence probes;
(c) washing away said population of unhybridized oligonucleotide sequence probes; and
(d) isolating said population of hybridized oligonucleotide sequence probes thereby forming an isolated population of hybridized oligonucleotide sequence probes, thereby cloning said nucleic acid from said biological sample, wherein said fixed biological sample comprises fixed cells.

2. The method of claim 1, further comprising the step of:
(e) amplifying said isolated population of hybridized oligonucleotide sequence probes to produce a population of amplified fragments comprising sequence tags.

3. The method of claim 2, further comprising sequencing said sequence tags in said population of amplified fragments comprising sequence tags.

4. The method of claim 1, wherein said biological sample is a pathological sample.

5. The method of claim 1, wherein said fixed biological sample is fixed by a method of fixation selected from the group consisting of formaldehyde, Bouin's, xylene and an ethanol precipitating fixative.

6. The method of claim 5, wherein said fixed biological sample is treated with a permeabilization agent prior to the hybridizing step.

7. The method of claim 6, wherein said permeabilization agent is selected from the group consisting of proteinase K, pronase and triethanolamine.

8. The method of claim 2, wherein said 5'-end extension sequence and said 3'-end extension sequence each comprise a restriction site for a class II restriction endonuclease or a homing endonuclease.

9. The method of claim 8, further comprising:
(f) cleaving said population of amplified fragments comprising sequence tags with said class II restriction endonuclease or homing endonuclease to produce cleaved fragments, and
(g) subcloning said cleaved fragments into a vector.

10. The method of claim 9, further comprising ligating said cleaved fragments comprising sequence tags together prior to said subcloning step.

11. The method of claim 1, wherein at least one of said 5'-end extension sequence and said 3'-end extension sequence comprises a detection sequence.

12. The method of claim 2, wherein said amplifying step comprises the polymerase chain reaction.

13. The method of claim 3, further comprising comparing sequences of said sequence tags to a database of gene sequences, thereby identifying one or more genes comprising said sequence tags.

14. The method of claim 1, wherein said biological sample is from a human.

15. The method of claim 2, further comprising hybridizing said population of amplified fragments comprising sequence tags to a microarray, thereby determining the sequences of the sequence tags.

16. The method of claim 15, further comprising comparing sequences of said sequence tags to a database of gene sequences, thereby identifying genes comprising said sequence tags.

17. A method of identifying a truncated mRNA sequence from a biological sample, wherein said biological sample is fixed, said method comprising:
(a) providing a population of oligonucleotide sequence probes, wherein each of said oligonucleotide sequence probes comprises a sequence tag flanked by a 5'-end extension sequence and a 3'-end extension sequence, wherein said 5'-end and 3'-end extension sequences are not found in the mammalian genome, further wherein said sequence tag is a degenerate sequence and wherein at least one of said 5'-end extension sequence and said 3'-end extension sequence comprises a detection sequence;
(b) hybridizing said population of oligonucleotide sequence probes with said nucleic acid in said biological sample, thereby forming a population of hybridized oligonucleotide sequences probes and a population of unhybridized oligonucleotide sequence probes;
(c) washing away said population of unhybridized oligonucleotide sequence probes;
(d) isolating said population of hybridized oligonucleotide sequence probes thereby forming an isolated population of hybridized oligonucleotide sequence probes,
(e) amplifying said isolated population of hybridized oligonucleotide sequence probes to produce a population of amplified fragments comprising sequence tags;
(f) annealing a detection oligonucleotide comprising a detectable label to at least one of said 5'-end extension sequence and said 3'-end extension sequence of each of said oligonucleotide sequence probe to form a population of detectably labeled amplified fragments, wherein said detection oligonucleotide is complementary to a detection sequence;
(g) hybridizing said population of detectably labeled amplified fragments to a microarray, wherein said microarray is capable of detecting sequences for at least two different regions of at least one mRNA;
(h) detecting the detectable label to obtain a signal for each of said at least two different regions of said at least one mRNA;

(i) comparing said signals from said at least two different regions of said at least one mRNA, whereby a difference in signal strength or an absence of a signal from one region and not another is indicative of a truncation in said mRNA, wherein the fixed biological sample comprises fixed cells.

\* \* \* \* \*

SEQUENCE LISTING

```
<160> NUMBER OF SEQ ID NOS: 10

<210> SEQ ID NO 1
<211> LENGTH: 56
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (7)..(26)
<223> OTHER INFORMATION: n is a, c, g, or t
<220> FEATURE:
<221> NAME/KEY: misc_feature
<222> LOCATION: (35)..(54)
<223> OTHER INFORMATION: n is a, c, g, or t

<400> SEQUENCE: 1
tcgaggnnnn nnnnnnnnnn nnnnnnccaa ttggnnnnnn nnnnnnnnnn nnnncc          56

<210> SEQ ID NO 2
<211> LENGTH: 56
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (51)..(51)
<223> OTHER INFORMATION: n is a, c, g, or t

<400> SEQUENCE: 2
tcgaggtttt ctattccccc aagagcccaa ttggcatttg tttcgggggg naggcc          56

<210> SEQ ID NO 3
<211> LENGTH: 56
<212> TYPE: DNA
<213> ORGANISM: Artificial
<220> FEATURE:
<223> OTHER INFORMATION: chemically synthesized

<400> SEQUENCE: 3
tcgaggacct cctatggcgc cttgtaccaa ttgggggatg gcaatgtgat gtaccc          56

<210> SEQ ID NO 4
<211> LENGTH: 56
<212> TYPE: DNA
<213> ORGANISM: Artificial
<220> FEATURE:
<223> OTHER INFORMATION: chemically synthesized

<400> SEQUENCE: 4
tcgaggactg gcccccata taacaaccaa ttgggggatg cttggtatag acgacc           56
```

```
<210> SEQ ID NO 5
<211> LENGTH: 56
<212> TYPE: DNA
<213> ORGANISM: Artificial
<220> FEATURE:
<223> OTHER INFORMATION: chemically synthesized

<400> SEQUENCE: 5
tcgaggatta tctccacgtc aactgcccaa ttggtgtttg acagtctttc gtgtcc        56

<210> SEQ ID NO 6
<211> LENGTH: 56
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (49)..(49)
<223> OTHER INFORMATION: n is a, c, g, or t

<400> SEQUENCE: 6
tcgaggacac gcaccctgac catacccaa ttggagaatg tctgtttgng aatgcc        56

<210> SEQ ID NO 7
<211> LENGTH: 96
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (39)..(58)
<223> OTHER INFORMATION: n is a, c, g, or t

<400> SEQUENCE: 7
acaaatctcc gttgtactgg atgcattacg taaattggnn nnnnnnnnn nnnnnnncc     60 tcgattagta gaacatccgg cattacgtat tttacc                             96

<210> SEQ ID NO 8
<211> LENGTH: 96
<212> TYPE: DNA
<213> ORGANISM: Artificial
<220> FEATURE:
<223> OTHER INFORMATION: chemically synthesized

<400> SEQUENCE: 8
acaaatctcc gttgtactgg atgcattacg taaattggaa gtagtgcggc acgtccggcc   60
tcgattagta gaacatccgg cattacgtat tttacc                             96

<210> SEQ ID NO 9
<211> LENGTH: 22
<212> TYPE: DNA
<213> ORGANISM: Artificial
<220> FEATURE:
<223> OTHER INFORMATION: chemically synthesized

<400> SEQUENCE: 9
acaaatctcc gttgtactgg at                                            22

<210> SEQ ID NO 10
<211> LENGTH: 23
<212> TYPE: DNA
<213> ORGANISM: Artificial
<220> FEATURE:
<223> OTHER INFORMATION: chemically synthesized
```

```
<400> SEQUENCE: 10
ggtaaaatac gtaatgccgg atg                                          23
```